(12) United States Patent
Yoon et al.

(10) Patent No.: US 11,273,117 B2
(45) Date of Patent: *Mar. 15, 2022

(54) WATER-IN-OIL POLYMERIC EMULSION COMPOSITION AND METHOD FOR MANUFACTURING WATER-IN-OIL POLYMERIC EMULSION COMPOSITION

(71) Applicants: KCI LIMITED, Seosan (KR); KER CHEMISTRY, SARL, Le Vesinet (FR)

(72) Inventors: Gwang Ho Yoon, Seoul (KR); Mae In Lee, Siheung (KR); Seong Gi Oh, Seoul (KR); Mallo Paul, Le Ve'sinet (FR)

(73) Assignees: KCI LIMITED, Seosan (KR); KER CHEMISTRY SARL, Le Vesinet (FR)

( * ) Notice: Subject to any disclaimer, the term of this patent is extended or adjusted under 35 U.S.C. 154(b) by 336 days.

This patent is subject to a terminal disclaimer.

(21) Appl. No.: 15/763,028

(22) PCT Filed: Feb. 24, 2016

(86) PCT No.: PCT/KR2016/001815
§ 371 (c)(1),
(2) Date: Mar. 23, 2018

(87) PCT Pub. No.: WO2017/052007
PCT Pub. Date: Mar. 30, 2017

(65) Prior Publication Data
US 2019/0054002 A1    Feb. 21, 2019

(30) Foreign Application Priority Data

Sep. 25, 2015   (KR) .................. 10-2015-0136662

(51) Int. Cl.
| | | |
|---|---|---|
| A61K 8/81 | (2006.01) | |
| A61K 8/06 | (2006.01) | |
| A61Q 19/00 | (2006.01) | |
| A61K 8/39 | (2006.01) | |
| A61K 8/33 | (2006.01) | |
| A61K 8/85 | (2006.01) | |
| A61K 8/04 | (2006.01) | |
| A61K 8/34 | (2006.01) | |
| A61K 8/36 | (2006.01) | |
| A61Q 5/02 | (2006.01) | |
| A61Q 5/12 | (2006.01) | |
| A61Q 19/10 | (2006.01) | |

(52) U.S. Cl.
CPC ............ *A61K 8/8158* (2013.01); *A61K 8/042* (2013.01); *A61K 8/064* (2013.01); *A61K 8/33* (2013.01); *A61K 8/345* (2013.01); *A61K 8/361* (2013.01); *A61K 8/39* (2013.01); *A61K 8/8188* (2013.01); *A61K 8/85* (2013.01); *A61Q 5/02* (2013.01); *A61Q 5/12* (2013.01); *A61Q 19/00* (2013.01); *A61Q 19/007* (2013.01); *A61Q 19/10* (2013.01); *A61K 2800/10* (2013.01); *A61K 2800/48* (2013.01)

(58) Field of Classification Search
CPC .. A61K 8/8188; A61K 8/064; A61K 2800/10; A61K 2800/48; A61K 8/8158
See application file for complete search history.

(56) References Cited

U.S. PATENT DOCUMENTS

| | | | |
|---|---|---|---|
| 5,883,181 A * | 3/1999 | Cicchiello | .............. C02F 1/54 210/732 |
| 5,914,366 A | 6/1999 | Cicchiello et al. | |
| 2006/0018852 A1* | 1/2006 | Fares | .............. A61K 31/56 424/62 |
| 2007/0141013 A1 | 6/2007 | Nguyen-Kim et al. | |
| 2010/0069592 A1 | 3/2010 | Matzuaki et al. | |
| 2014/0213748 A1 | 7/2014 | Blondel et al. | |

FOREIGN PATENT DOCUMENTS

WO    2013108174 A1    7/2013

OTHER PUBLICATIONS

Graeber ("A study of Fundamentals in Emulsion Templating for the Preparation of Macroporous Polymer Foams"; 2013; PhD Dissertation; file:///C:/Users/tthomas2/Downloads/Graeber-N-2013-PhD-Thesis.pdf; accessed Nov. 20, 2020 (Year: 2013).*
International Search Report for International Patent Application No. PCT/KR2016/001815, dated May 31, 2016.

* cited by examiner

Primary Examiner — Timothy P Thomas

(57) ABSTRACT

The present invention provides a water-in-oil polymeric emulsion composition, including: (a) 25 to 65 wt % of a cross-linked polymer; (b) 15 to 40 wt % of an oil; (c) 1 to 12 wt % of a surfactant; and (d) 1 to 40 wt % of water, wherein (a) the cross-linked polymer is polymerized by using 35 to 85 mol % of a 2-acrylamido-2-methylpropane-sulfonic acid totally or partially salified by an alkali metal or ammonium, 10 to 50 mol % of acryloyl morpholine, 2 to 25 mol % of an acrylic acid totally or partially salified by an alkali metal or ammonium, and 0.005 to 1 mol % of a polyethylenic monomer used as a cross-linking agent.

22 Claims, No Drawings

WATER-IN-OIL POLYMERIC EMULSION COMPOSITION AND METHOD FOR MANUFACTURING WATER-IN-OIL POLYMERIC EMULSION COMPOSITION

CROSS-REFERENCE TO RELATED APPLICATIONS

The present specification is a U.S. National Stage of International Patent Application No. PCT/KR2016/001815 filed Feb. 24, 2016, which claims priority to and the benefit of Korean Patent Application No. 10-2015-0136662 filed in the Korean Intellectual Property Office on Sep. 25, 2015, the entire contents of which are incorporated herein by reference.

TECHNICAL FIELD

The present invention relates to a water-in-oil polymeric emulsion composition and a method for manufacturing a water-in-oil polymeric emulsion composition, and, more particularly, to a water-in-oil polymeric emulsion composition being used for a cosmetic formulation and a pharmaceutical formulation and a cosmetic and a pharmaceutical formulations containing the water in oil polymeric emulsions of the invention.

BACKGROUND ART

Various thickeners for manufacturing a skincare product, a hair care product, or a cosmetic, dermo-cosmetic, or pharmaceutical composition is publicly known. Thickeners may be largely classified into natural products and synthetic polymers. For the natural products, such as, guar gum, corn starch, or so on, there are disadvantages, such as, price fluctuations, supply problems, and difficulties for uniform quality maintenance. Accordingly, the natural products may be difficult to be industrially used.

Since the synthetic polymer that is generally used is in a solid state such as a powder including an acid functional group, the synthetic polymer should be dispersed in a solution in advance in order to achieve thickening effect, and a neutralization process for the acid functional group is necessary due to pH dependent property of the synthetic polymer; Carbopol and Pemulen are example of these kind of powders. There are also synthetic polymers as powders, such as, Aristoflex and Sepinov for which acid group is already neutralized. However, for these synthetic polymers in powder form, stirring for a long time is necessary and a great care for preventing aggregation and coagulation (or solidification) is necessary in order to produce a uniform solution. In addition, the dust is caused and thus a dust collecting system and personal protective equipment are necessary. Also, the dissolution may be difficult according to states and conditions that the synthetic polymers are used.

In order to overcome defects of the synthetic polymers in powder form, water-in-oil emulsion thickeners have been developed. The water-in-oil emulsion thickeners are easily mixed when they are used for a cosmetic product and so on. Also, since the water-in-oil emulsion thickeners are polymerized after neutralizing an acid functional group, a process for neutralizing the acid functional group is not necessary, unlike most of the synthetic polymers in powder form The polymers contained in the water in oil emulsions are generally copolymer of acrylamide/alkali metal acrylate or copolymer of acrylamide/sodium 2-acrylamido-2-methyl-propane-sulfonate. They are already neutralized. For example, when they are dissolved in water with a concentration of 1%, pH of them are generally 6 or more.

As water-in-oil polymeric emulsion thickener, a material having the most efficiency is a copolymer of acrylamide/sodium 2-acrylamido-2-methylpropane-sulfonate. This copolymer is described in European Patent No. 0503853.

The water-in-oil polymeric emulsion thickener has a useful viscosity in a large range of pH (for example, pH of 3 to 12). The viscosity of the water-in-oil polymeric emulsion thickener can be maintained with a high efficiency in water containing electrolytes (salt) used for cosmetic industry, The water-in-oil polymeric emulsion thickener is able to stabilize (or "emulsify") various kinds of oils. Particularly, the emulsified cosmetic formulations have stability even at a high temperature.

However, the thickener is polymerized from an acrylamide monomer. In cosmetic industry and pharmaceutical industry, frequency in use of a material including acrylamide as a monomer decreases. The residues of the acrylamide are restricted by regulations according to areas. Nevertheless the use of acrylamide in cosmetic and pharmacy industries is in practice banned for new products as the restrictions and end users pressure are too strong.

In order to avoid the use of the copolymer of acrylamide/sodium 2-acrylamido-2-methylpropane-sulfonate as a water-in-oil polymeric emulsion thickener, new water-in-oil polymeric emulsion thickeners not using the acrylamide have been developed. The most effective products among the thickeners are as follows:

A copolymer of sodium acrylate/sodium 2-acrylamido-2-methylpropane-sulfonate is stated in European Patent No. 1047716, a copolymer of Hydroxyethyl acrylate/sodium 2-acrylamido-2-methyl propane-sulfonate is stated in European Patent No. 1369435, a polymer of sodium 2-acrylamido-2-methyl propane-sulfonate is stated in European Patent No. 1056805, a copolymer of dimethyl acrylamide/sodium 2-acrylamido-2-methyl propane-sulfonate is stated in European Patent No. 1726600, and a copolymer of sodium acrylate/beheneth 25 methacrylate is stated in PCT publication No. WO 02/100374.

The above water-in-oil polymeric emulsion thickeners do not include acrylamide monomer but their efficiencies thereof is lower than the copolymer of acrylamide/sodium 2-acrylamido-2-methylpropane-sulfonate.

According to descriptions stated in European Patent No. 1047716, thickening effect is low in a condition of pH 5 or less in a case of the water-in-oil emulsion copolymer of sodium acrylate/sodium 2-acrylamido-2-methylpropane-sulfonate. According to descriptions stated in European Patent No. 1056805, viscosity is very low in water containing electrolytes (salt) in a case of the polymer of sodium 2-acrylamido-2-methylpropane-sulfonate. According to descriptions stated in PCT publication No. WO 02/100374, it is impossible to increase viscosity in a condition of pH 6 or less in a case of the water-in-oil emulsion copolymer of sodium acrylate/beheneth 25 methacrylate. According to descriptions stated in European Patent No. 1369435, effect for increasing viscosity is low in water containing electrolytes (salt) in a case of the water-in-oil emulsion copolymer of Hydroxyethyl acrylate/sodium 2-acrylamido-2-methyl-propane-sulfonate, and chemical stability of the Hydroxyethyl acrylate is low in a condition of pH 8 or more. Also, according to descriptions stated in European Patent No. 1726600, in the case of the copolymer of dimethyl acrylamide/sodium 2-acrylamido-2-methylpropane-sulfonate, viscosity of a solution in water containing electrolytes (salt)

are low compared with the conventional materials. Also, the fact that an 'acrylamide derivative' (dimethyl acrylamide) is used as monomer should be problem for the final customers.

A simple ester monomer, such as, hydroxyl ethyl acrylate, may be hydrolyzed depending on pH and due to a high temperature. Also, the simple ester monomer may be transformed into unknown impurities or properties of a thickener may be varied by the hydrolysis. The fact may potentially affect stability of cosmetic products. A thickener using the hydroxyethyl acrylate is stated in European Patent No. 1369435.

DISCLOSURE OF INVENTION

Technical Problem

[15] It is an object of the present invention to provide a water-in-oil polymeric emulsion composition having excellent effect in increasing viscosity even in a condition of low pH, a good salt tolerance and not including acrylamide and being able to be stable versus degradation with time (hydrolysis, chemical reaction and so on). It is also other object to provide a method to manufacture a water in oil polymeric emulsion composition, to provide its uses and to provide cosmetic, pharmaceutical and dermo pharmacy formulations containing it.

However, objects of the present invention are not limited to the above-mentioned object, and other objects that are not stated will be understood from the following descriptions by a skilled person in the art.

Solution to Problem

The present invention provides a water-in-oil polymeric emulsion composition, including:
(a) 25 to 65 wt % of a cross-linked polymer;
(b) 15 to 40 wt % of at least one oil; and
(c) 1 to 12 wt % of a least one surfactant or polymeric surfactant; and
(d) 1 to 40 wt % of water,
wherein (a) the cross-linked polymer is polymerized by using 35 to 85 mol % of a 2-acrylamido-2-methylpropane-sulfonic acid totally or partially salified by an alkali metal or ammonium, 10 to 50 mol % of acryloyl morpholine, 2 to 25 mol % of an acrylic acid totally or partially salified by an alkali metal or ammonium, and 0.005 to 1 mol % of a polyethylenic monomer used as a cross-linking agent.

The present invention provides a method for manufacturing a water-in-oil polymeric emulsion composition, including steps of:
(S1) forming an aqueous-phase by mixing a cross-linking agent, and a 2-acrylamido-2-methylpropane-sulfonic acid totally or partially salified by an alkali metal or ammonium, acryloyl morpholine, and an acrylic acid totally or partially salified by an alkali metal or ammonium and dissolving them into water;
(S2) forming an oil-phase by mixing an oil and a surfactant and or polymeric surfactant having a HLB of 3 to 7;
(S3) forming a water in oil emulsion by adding the aqueous-phase into the oil-phase and stirring them; and
(S4) polymerizing the water-in-oil emulsion by adding a radical initiator into the water in oil emulsion.

The present invention also describes the use of a composition of the invention as thickener and or stabilizer (emulsifier) for water phase and more particularly for cosmetic or dermo-cosmetic or pharmaceutical formulations containing a water phase.

The present invention also claims cosmetic or dermo-cosmetic or pharmaceutical formulations containing a water in oil polymeric composition of the invention.

SUMMARY OF THE INVENTION

The first object of the present invention provides a water-in-oil polymeric emulsion composition that is manufactured by forming a water-in-oil emulsion through stirring an aqueous-phase and an oil-phase with a high speed and emulsifying them, and performing a polymerization reaction. The water-in-oil polymeric emulsion composition according to the present invention includes a cross-linked polymer. The water-in-oil polymeric emulsion composition according to the present invention may be stabilized by a surfactant and or a polymeric surfactant having a low HLB (hydrophile-lipophile balance), and a surfactant having a high HLB in some cases.

The second object of the present invention provides a method for manufacturing a water-in-oil polymeric emulsion composition.

The third object of the present invention relates to the use of the water in oil polymeric emulsion compositions mentioned above to thicken and or stabilize a formulation comprising at least an aqueous phase and more particularly cosmetic or dermo-cosmetic or pharmaceutical formulations.

Also, the water-in-oil polymeric emulsion composition according to the present invention used for a thickener or a stabilizer can be suitably applied to a cosmetic, dermo-cosmetic, or pharmaceutical product (or formulations) having pH of a large range from low pH to high pH (for example, pH 3 to 12). Also, the water-in-oil polymeric emulsion composition according to the present invention can be suitably applied to a cosmetic, dermo-cosmetic, or pharmaceutical product including water containing electrolytes, such as, NaCl, KCl, $CaCl_2$), or $MgSO_4$, or to a cosmetic, dermo-cosmetic, or pharmaceutical product including a compound having high reactivity, such as, peroxides, oxidants, aldehydes, preservatives, and so on. The water-in-oil polymeric emulsion composition according to the present invention may be very effectively used with a surfactant or another (natural or synthetic) thickener.

Particularly, when the water-in-oil polymeric emulsion composition according to the present invention is used for a cosmetic, dermo-cosmetic, or pharmaceutical formulations, it is highly suitable to be used with alpha and beta hydroxyl acids, such as, a glycolic acid, a lactic acid, a salicylic acid, a kojic acid, and so on; self tanning agents, such as, dihydroxy acetone; anti-acne agents or anti-aging agents such as retinol and so on; sliming agents, such as, caffeine and so on; anti-wrinkle agents; lightening agents; anti-dark-circles agents; and other actives agents.

Also, the present invention provides a water-in-oil polymeric emulsion composition suitable to be used for a cosmetic, dermo-cosmetic, or pharmaceutical formulations including a material of a sun cream (or a sunscreen material), such as, octocrylene, octyl para-methoxycinnamate, avobenzone, benzophenone, methylbenzylidene camphor, a titanium dioxide, a zinc oxide, a phenylbenzimidazole sulfonic acid, and so on.

In addition, the present invention provides a water-in-oil polymeric emulsion composition suitable to be used for a cosmetic, dermo-cosmetic, or pharmaceutical formulations including an emulsifier material, such as, fatty acids, fatty alcohols, ethoxylated fatty acids, ethoxylated fatty alcohols, fatty esters, polysorbates, polyglycerol esters, alkyl polyglucosides, sucrose esters, and so on.

Further, the present invention provides a water-in-oil polymeric emulsion composition suitable to be used for a cosmetic, dermo-cosmetic, or pharmaceutical composition including an oil absorber material, such as, silica, polymethyl methacrylate, polyamide (nylon), mica, polyethylene, and so on.

The fourth object of the present invention provides a cosmetic formulation, a dermatological formulation, or a pharmaceutical formulation, including the above water-in-oil polymeric emulsion composition of the invention in amount of 0.1 to 10 wt %.

Yet still further, the water-in-oil polymeric emulsion composition according to the present invention can be used for various formulations or types, such as, a gel type, a cream type, a lotion type, an emulsion type, a soap type, a spray type, and so on.

DETAILED DESCRIPTION OF THE PREFERRED EMBODIMENTS

Before describing the present invention in detail, it should be understood that terms used in this specification are used only for describing a certain embodiment and do not limit the present invention that is limited only by attached claims. All technical terms and scientific terms used in this specification have meanings the same as meanings that are generally understood by a skilled person in the art, unless otherwise specifically stated.

In the entire specification and claims, terms of "comprise", "comprises", "comprising", "include", "includes", or "including" means that the thing, the step, the group of things, or the steps are just included and does not exclude other thing, other step, other group of things, or other steps, unless otherwise specifically stated.

Meanwhile, an embodiment of the present invention may be combined with another embodiment of the present invention, unless otherwise specifically stated. Particularly, a technical feature that is stated to be preferable or advantageous may be combined with another technical feature that is stated to be preferable or advantageous. Hereinafter, embodiments of the present invention and effects thereof will be described with reference to the accompanying drawings.

The present invention relates to a water-in-oil (W/O type) polymeric emulsion composition. The water-in-oil polymeric emulsion composition according to the present invention includes (a) a cross-linked polymer (more exactly a cross-linked anionic polymer), (b) at least one oil, (c) at least one surfactant or a polymeric surfactant, and (d) water.

The water-in-oil polymeric emulsion composition includes (a) 25 to 65 wt % of the cross-linked polymer, (b) 15 to 40 wt % of at least one oil, (c) 1 to 12 wt % of a least one surfactant or a polymeric surfactant, and (d) 1 to 40 wt % of the water.

Preferably, the water-in-oil polymeric emulsion composition includes (a) 30 to 50 wt % of the cross-linked polymer, (b) 20 to 30 wt % of at least one oil, (c) 2 to 10 wt % at least one surfactant or a polymeric surfactant, and (d) 15 to 35 wt % of the water.

(a) The cross-linked polymer generally includes a non-linear polymer that is swellable in water although it is insoluble in water. The cross-linked polymer according to the present invention may be cross-linked and polymerized by the after-mentioned monomer (preferably, a polyethylenic monomer) used as a cross-linking agent.

(a) The cross-linked polymer is polymerized by using 2-acrylamido-2-methylpropane-sulfonic acid (AMPS) totally or partially salified by an alkali metal or ammonium, acryloyl morpholine (ACMO), an acrylic acid (AA) totally or partially salified by an alkali metal or ammonium, and 0.005 to 1 mol % of a polyethylenic monomer as a cross-linking agent.

(a) The cross-linked polymer is polymerized by using 35 to 85 mol % of the AMPS totally or partially salified by the alkali metal or ammonium, 10 to 50 mol % of the ACMO, 2 to 25 mol % of the AA totally or partially salified by the alkali metal or ammonium, and 0.005 to 1 mol % (as mole of cross-linker by mole of monomer) of the polyethylenic monomer.

Preferably, (a) the cross-linked polymer is polymerized by using 40 to 80 mol % of the AMPS totally or partially salified by the alkali metal or ammonium, 15 to 45 mol % of the ACMO, 2 to 15 mol % of the AA totally or partially salified by the alkali metal or ammonium, and 0.005 to 1 mol % of the polyethylenic monomer. More preferably, (a) the cross-linked polymer is polymerized by using 50 to 70 mol % of the AMPS totally or partially salified by the alkali metal or ammonium, 20 to 40 mol % of the ACMO, 2 to 10 mol % of the AA totally or partially salified by the alkali metal or ammonium, and 0.005 to 1 mol % of the polyethylenic monomer.

The AMPS totally or partially salified by the alkali metal or ammonium may be preferably AMPS totally or partially salified by sodium, and the AA totally or partially salified by the alkali metal or ammonium may be preferably AA totally or partially salified by sodium.

The polyethylenic monomer may include at least one selected from the group consisting of methylene-bis-acrylamide, ethylene glycol dimethacrylate, diethylene glycol dimethacrylate, triallyl amine, trimethylol propane tri(meth)acrylate, diallyl urea, tetraallyl oxy ethane, diallyl oxy acetic acid, allyl penta erythritol, allyl sucrose, and trimethylolpropane diallyl ether.

Preferably, the polyethylenic monomer may include methylene-bis-acrylamide, triallyl amine, or a mixture thereof.

The polyethylenic monomer may be included preferably in an amount of 0.01 to 0.6 mol %, and the polyethylenic monomer may be more preferably included in an amount of 0.01 to 0.4 mol %.

(b) The oil may include at least one selected from the group consisting of:

a mineral oil including isoparaffin having $C_8$ to $C_{16}$, (Isopar G, H, L, M, V, or so on made by Exxon chemical), isohexadecane, or isododecane;

a white mineral oil (Marcol 52/82 or so on);

a synthetic oil including polyisobutene or polyisodecene;

a natural oil including fatty alcohol ethers, such as, dioctyl ether, didecyl ether, or so on;

a natural oil including fatty esters, such as, octyl palmitate, triglyceride, cococaprylate caproate, hexyl stearate, or so on; and squalane.

More preferably, (b) the oil includes a natural oil of fatty alcohol ether or fatty ester. Most preferably, (b) the oil includes dioctyl ether.

(c) The surfactant may include a surfactant having a HLB (hydrophilic-lipophilic balance) of 3 to 7 and or a polymeric surfactant having a HLB of 3 to 7.

The surfactant having the HLB (hydrophilic-lipophilic balance) of 3 to 7 may be sorbitan ester as sorbitan monooleate, sorbitan isostearate, sorbitan sesquioleate or dialkanolamide. Preferably, sorbitan ester may be used.

Also, the polymeric surfactant has low molecular weight and has surface properties like a surfactant. Hypermer 1083, Hypermer 2296, Hypermer B 246, Hypermer B261, or so on made by Croda may be used as the polymeric surfactant. Preferably, the polymeric surfactant having the HLB of 3 to 7 comprises a block copolymeric ester of a 12-hydroxystearic acid and ethyleneglycol as Hypermer B246. These block copolymers are described in U.S. Pat. No. 4,203,877.

Also, the water-in-oil polymeric emulsion composition according to an embodiment of the invention may further include a surfactant having a high HLB of 10 to 16. The water-in-oil polymeric emulsion composition may be stabilized by the surfactant having the high HLB of 10 to 16. This surfactant having the high HLB of 10 to 16 may be included or may be not included in the water-in-oil polymeric emulsion composition. If the surfactant having the high HLB is used, it may be preferably added after a polymerization reaction that will be described later. However, according to occasions, the surfactant having the high HLB may be used for the water-in-oil polymeric emulsion composition before the polymerization reaction that will be described later.

For the surfactant having the high HLB of 10 to 16, ethoxylated sorbitan ester (for example, sorbitan oleate ethoxylated with 20 moles of an ethylene oxide or sorbitan oleate ethoxylated with 5 moles of an ethylene oxide), ethoxylated fatty alcohol (for example, lauryl alcohol ethoxylated with 7 moles of an ethylene oxide or oxo C13 and 6 moles of an ethylene oxide), polyglycerol ester (for example, decaglycerol mono oleate, decaglycerol dioleate, decaglycerol monolaurate or decaglycerol dilaurate), alkyl polyglucoside (caprylyl/capric glucoside) may be used.

Preferably, for the surfactant having the high HLB of 10 to 16, the polyglycerol ester or the alkyl polyglucoside may be used. More preferably, for the surfactant having the high HLB of 10 to 16, the decaglycerol dilaurate may be used.

The surfactant having the HLB of 10 to 16 may be included in an amount of 1 to 6 wt %. More preferably, the surfactant having the HLB of 10 to 16 may be included in an amount of 3 to 5 wt %.

The water-in-oil polymeric emulsion composition according to an embodiment of the present invention may be manufactured by emulsifying an aqueous-phase into an oil-phase and performing a polymerization reaction in using a radical initiator.

The second object of present invention is a method for manufacturing a water-in-oil polymeric emulsion composition according to an embodiment of the present invention includes (S1) forming an aqueous-phase by mixing a monomer, a cross-linking agent, and water, (S2) forming an oil-phase by mixing an oil and a surfactant, (S3) forming an water in oil emulsion by adding the manufactured aqueous-phase into the manufactured oil-phase and stirring them, and (S4) polymerizing the water-in-oil emulsion by adding a radical initiator into the water in oil emulsion.

In the step (S1) of forming the aqueous-phase, the aqueous-phase is manufactured by mixing one or more cross-linking agent, the AMPS salified by the alkali metal or ammonium, the ACMO, and the AA salified by the alkali metal or ammonium as monomers and dissolving them in the water.

The ratio of the monomers, cross-linkers and water are those described above for the water in oil composition of the invention.

The manufactured aqueous-phase has pH of 4 to 7.

In the step (S2) of forming the oil-phase, the oil-phase is manufactured by mixing the oil and the surfactant. The amount and the kind of the oil may be the same as the amount and the kind of the oil included in the above-described water-in-oil polymeric emulsion composition, and the amount and the kind of the surfactant may be the same as the amount and the kind of the surfactant or the polymeric surfactant having the low HLB of 3 to 7 included in the above-described water-in-oil polymeric emulsion composition.

In the step (S3) of forming the water in oil emulsion where the aqueous-phase is emulsified into the oil-phase is manufactured by adding the aqueous-phase into the oil-phase and stirring them with a high speed (for example, with a rotation speed of 4,000 to 8,000 rpm) for 10 to 30 minutes.

In the step (S4) of polymerizing the water-in-oil emulsion, oxygen is eliminated by injecting nitrogen and the polymerization is induced by a thermal decomposition reaction or a redox reaction through introducing a radical initiator. In the step (S4) of polymerizing the water-in-oil emulsion, the polymerization is preferably started or initiated at a temperature of 20° C. or less and is completed at a temperature of 65° C. or more by an exothermic reaction through a redox initiator.

The method for manufacturing the water-in-oil polymeric emulsion composition according to the embodiment of the present invention may further include a step (S5) of stabilizing the water-in-oil polymeric emulsion by adding the surfactant having the high HLB into the water-in-oil polymeric emulsion composition where the reaction is completed.

Also, the method for manufacturing the water-in-oil polymeric emulsion composition according to the embodiment of the present invention may further include a step of (S6) concentrating the water-in-oil polymeric emulsion by evaporating a part of the water and a part of the oil included in the water-in-oil polymeric emulsion composition.

The third object of the present invention relates to the use of the water in oil polymeric emulsion compositions mentioned above to thicken and or stabilize a formulation comprising at least an aqueous phase and more particularly cosmetic or dermo-cosmetic or pharmaceutical formulations.

The present invention provides as fourth object aqueous formulations and more particularly a cosmetic, dermo-cosmetic or pharmaceutical formulations including the water-in-oil polymeric emulsion composition manufactured according to the embodiment of the present invention in an amount of 0.1 to 10 wt %.

EMBODIMENTS

Embodiment 1

(1) Manufacturing of the Aqueous-Phase

① 183.5 g of ion-exchange water (or a deionized water) was added into and stirred in 1000 ml beaker. ② 105.6 g of a 50% NaOH solution was added and mixed. ③ 273.3 g of 2-acrylamido-2-methylpropanesulfonic acid (AMPS) was added and dissolved. ④ 0.2 g of sodium diethylenetriaminepentaacetate was added. ⑤ 77.6 g of acryloyl morpholine (ACMO) and 23.8 g of an acrylic acid (AA) were added and mixed. ⑥ 1.0 g of triallylamine was added and the solution was neutralized by using 15 g of a 50% NaOH solution. ⑦ Ion-exchange water was added in order to make the solution having a weight of 680 g.

(2) Manufacturing of the Oil-Phase

① 235 g of dioctyl ether was added into and stirred in 1000 ml beaker. ② 25 g of Hypermer 1083 (sold by CRODA and known to be a mixture of sorbitan oleate and block copolymeric ester of a hydroxystearic acid and ethyleneglycol, so a mixture of conventional surfactant and polymeric surfactant) was added and mixed. ③ 0.2 g of azobisisobutyronitrile was added and dissolved.

(3) Manufacturing of the Water-In-Oil Emulsion

③ The aqueous-phase was added into the manufactured oil-phase and was strongly stirred with a rotation speed of 7000 rpm by a homogenizer. ② The mixture was stirred with the rotation speed of 7000 rpm for about 20 minutes, and a homogeneous water-in-oil emulsion was manufactured.

(4) Polymerization Reaction

① The manufactured water-in-oil emulsion was transferred to 1000 ml flask for a reaction equipped with an agitator (or a mixer), a thermometer, an inlet for nitrogen, and an inlet for catalyst were installed. ② Nitrogen was introduced into the water-in-oil emulsion for 1 hour while the water-in-oil emulsion was stirred with a rotation speed of 200 rpm to eliminate oxygen. ③ The temperature of the water-in-oil emulsion was adjusted to 15° C., and 0.023 g of cumene hydroperoxide was mixed with 4 g of dioctyl ether, and then, the mixed materials were added into the water-in-oil emulsion. ④ The mixture was stirred for 5 minutes, and a sodium metabisulfite solution (0.375 g of sodium bisulfite in 100 g of $H_2O$) was added into the reaction container with a speed of 0.3 ml per minute. ⑤ After ten minutes of adding the sodium metabisulfite solution, an exothermic reaction was started and the temperature was reached to 75° C. after 20 minutes. ⑥ The sodium metabisulfite solution was continuously added for 20 minutes and the temperature was maintained in 75° C. for 1 hour. ⑦ The mixture was cooled to 40° C., and then, 42.4 g of decaglycerol dilaurate (KCI PGLLA210KC) was added and mixed. ⑧ The final product was a water in oil polymeric emulsion. The neat viscosity of the water-in-oil polymeric emulsion was 4000 mPa·s (Brookfield RVT, spindle no 3, 20 rpm, 25° C.), and the viscosity of a 2% solution into water thereof was 80 000 mPa·s (Brookfield RVT, spindle no 6, 5 rpm, 25° C.).

Embodiment 2 to Embodiment 4

Water-in-oil polymeric emulsion compositions were manufactured by the same method as the method in Embodiment 1, except that amounts of raw materials in the aqueous-phase were changed as stated in Table 1.

TABLE 1

| (UNIT: g) | Embodiment 1 | Embodiment 2 | Embodiment 3 | Embodiment 4 |
|---|---|---|---|---|
| Ion-exchange water | 183.5 | 162.28 | 180.87 | 162.08 |
| 50% sodium hydroxide solution | 105.6 | 114.4 | 105.6 | 114.4 |
| AMPS | 273.3 | 296 | 273.3 | 296 |
| Sodium diethylenetri-aminepenta-acetate | 0.2 | 0.2 | 0.2 | 0.2 |
| ACMO | 77.6 | 93.17 | 93.17 | 93.17 |
| Acrylic acid | 23.8 | 7.93 | 15.86 | 7.93 |
| Triallylamine | 1 | 1 | 1 | 1.2 |
| 50% sodium hydroxide solution | 15 | 5.02 | 10 | 5.02 |
| Total weight after additionally adding ion-exchange water | 680 | 680 | 680 | 680 |

The final characteristics of the products corresponding to embodiments 2 to 4 are gathered in the table 2

Embodiment 5

(1) Manufacturing of the Aqueous-Phase

The aqueous-phase was manufactured by the same method as stated in Embodiment 1 except that 0.1 g of methylene-bis-acrylamide was added instead of 1.0 g of triallyl amine.

(2) Manufacturing of the Oil-Phase

The oil-phase was manufactured by the same method as stated in Embodiment 1 except that 0.2 g of azobisisobutyronitrile was not added.

(3) Manufacturing of the Water-In-Oil Emulsion

The water-in-oil emulsion was manufactured by the same method as stated in Embodiment 1.

(4) Polymerization Reaction

The water-in-oil polymeric emulsion was manufactured by the same method as stated in Embodiment 1 except for the following:
The temperature of the water-in-oil emulsion was adjusted to 15° C., and 0.3 g of ammonium persulfate was dissolved in 4 g of water and the mixture was added into the water-in-oil emulsion. After 5 minutes, a mixture of 0.023 g of cumene hydroperoxide mixed with 4 g of dioctyl ether was added.
The final product was a water in oil polymeric emulsion.
The characteristics of the final products are gathered in Table 2.

Embodiment 6

The water in oil polymeric emulsion composition is manufactured as in embodiment 5 except the manufacturing of oil phase
The oil phase is made of 235 g of dioctyl ether, 19 g of sorbitan oleate and 6 g of Hypermer B 246 (sold by CRODA and known to be a block copolymeric ester of a hydroxystearic acid and ethyleneglycol). The characteristics of the final product are gathered below in Table 2

(1) Characteristics of the Water in Oil Polymeric Emulsions of the Invention

The viscosities of the neat water in oil polymeric emulsions of the invention were measured by a Brookfield RVT viscometer at a temperature of 25° C. (spindle no 3, 20 rpm). The results are shown in Table 2.

The viscosities of 2% water in oil polymeric emulsions of the invention into water were measured by a Brookfield RVT viscometer at a temperature of 25° C. (spindle 6 at 5 rpm).

The pH of these above 2% aqueous solutions are also measured.

The viscosities of 3% water in oil polymeric emulsion of the invention into water containing 0.1% NaCl are measured by a Brookfield RVT viscometer at a temperature of 25° C. (spindle 6 at 5 rpm).

viscosities (IV). The cosmetic emulsions were stored in a chamber of 50° C. for 30 days, and then, stabilities (S) were confirmed. That is, whether the oil was separated or not was confirmed. If the oil was not separated, it was determined to be "stable". The results are shown in Table 4.

TABLE 2

| (UNIT: mPa · s) | Embodiment 1 | Embodiment 2 | Embodiment 3 | Embodiment 4 | Embodiment 5 | Embodiment 6 |
|---|---|---|---|---|---|---|
| Viscosity of emulsion | 4000 | 3800 | 3500 | 4300 | 4800 | 4700 |
| Viscosity of 2% solution | 80000 | 78000 | 63000 | 81000 | 82000 | 81000 |
| pH of 2% solution | 6.45 | 6.15 | 6.25 | 6.32 | 6.65 | 6.60 |
| Viscosity of 3% solution and 0.1% NaCl | 24000 | 21600 | 24000 | 22600 | 24000 | 24000 |

(2) Viscosities According to pH

Viscosities of 3% solutions of the water-in-oil polymeric emulsion compositions obtained in Embodiments 1 to 6 according to pH were measured by a Brookfield RVT viscometer at a temperature of 25° C. (spindle no 6, 5 rpm). The results are shown in Table 3.

TABLE 3

| (UNIT: mPa · s) | | Embodiment 1 | Embodiment 2 | Embodiment 3 | Embodiment 4 | Embodiment 5 | Embodiment 6 |
|---|---|---|---|---|---|---|---|
| Viscosity of 3% solution | pH 11.0 | 98000 | 70000 | 72000 | 80000 | 74000 | 74000 |
| | pH 10.0 | 100000 | 88000 | 75000 | 102000 | 98000 | 89000 |
| | pH 9.0 | 110000 | 92000 | 82000 | 108000 | 100000 | 100000 |
| | pH 6.0 | 110000 | 101000 | 84000 | 113000 | 108000 | 108000 |
| | pH 5.0 | 86000 | 94000 | 70000 | 109000 | 106000 | 106000 |
| | pH 4.0 | 78000 | 90000 | 66000 | 100000 | 102000 | 102000 |
| | pH 3.0 | 62000 | 70000 | 60000 | 82000 | 80000 | 80000 |

(3) Stabilizing (or Emulsifying) Properties of the Embodiments 1 to 6

3 g of the water-in-oil emulsion compositions manufactured by Embodiments 1 to 6 was stirred and dissolved in 87 g of water (ion-exchange water), and then, each of 10 g of oils stated in Table 4 was added, stirred, and emulsified, and thus, cosmetic emulsions were manufactured. Viscosities (V) were measured by a Brookfield RVT viscometer at a temperature of 25° C. (spindle no 6, 5 rpm) as initial

TABLE 4

| | (UNIT: mPa · s) | | Embodiment 1 | Embodiment 2 | Embodiment 3 | Embodiment 4 | Embodiment 5 | Embodiment 6 |
|---|---|---|---|---|---|---|---|---|
| V | Liquid paraffin | IV | 80000 | 79000 | 64000 | 81000 | 78000 | 79000 |
| | | S | stable | stable | stable | stable | stable | stable |
| | Dimethicone | IV | 90000 | 89000 | 75000 | 92000 | 91000 | 91000 |
| | | S | stable | stable | stable | stable | Stable | stable |
| | Cyclomethicone | IV | 85000 | 85000 | 72000 | 88000 | 86000 | 85000 |
| | | S | stable | stable | stable | stable | Stable | stable |
| | Jojoba oil | IV | 111000 | 102000 | 85000 | 105000 | 114000 | 115000 |
| | | S | stable | stable | stable | stable | stable | stable |
| | Caprylic/Capric triglyceride | IV | 110000 | 103000 | 87000 | 108000 | 112000 | 113000 |
| | | S | stable | stable | stable | stable | stable | stable |

(4) Stability of the Cosmetic Formulations Based on the Water in Oil Polymeric Emulsions of the Invention in Presence of Hydrogen Peroxide and in Presence of Dihydroxyacetone The stability of the viscosities (VP) in presence of hydrogen peroxide was confirmed. Particularly, 2 g of the water-in-oil polymeric emulsion composition manufactured by each of Embodiments 1 to 6, 2 g of hydrogen peroxide, and 96 g of water were mixed. Initial viscosity (IV) and viscosity (SV) after one-month storage at a temperature of 40° C. were measured. Also, when ratio (RV) of viscosity variations [{(initial viscosity (IV))−(viscosity (SV) after the one-month storage)}×100/(initial viscosity (IV))] are 5% or less, the viscosity in presence of hydrogen peroxide is decided to be stable.

Color stabilities (CS) in presence of dihydroxyacetone were confirmed. Particularly, 2 g of the water-in-oil polymeric emulsion composition manufactured by each of Embodiments 1 to 6, 5 g of dihydroxyacetone, and 93 g of water were mixed and a color change was confirmed after one-month storage at a temperature of 40° C. When the color is white to yellow, it is decided to be good. When the color is yellow, it is decided to be normal. When the color is brown, it is decided to be not good.

The results are shown in Table 5.

TABLE 5

| | | Embodiment 1 | Embodiment 2 | Embodiment 3 | Embodiment 4 | Embodiment 5 | Embodiment 6 |
|---|---|---|---|---|---|---|---|
| VP | IV (unit: mPa · s) | 80000 | 78000 | 63000 | 81000 | 82000 | 82000 |
| | SV (unit: mPa · s) | 78000 | 77000 | 62000 | 81000 | 80000 | 80000 |
| | RV | 2.5% | 1.3% | 1.6% | 0% | 2.4% | 2.4% |
| | stability | stable | stable | stable | stable | stable | stable |
| CS | | good | good | good | good | good | good |

(5) Comparative Examples B, C, D

The viscosity properties of the water-in-oil polymeric emulsion composition obtained in Embodiment 1 (Example A below) and of the other water-in-oil emulsion polymeric thickeners of the prior art were measured according various test condition. Viscosities were measured by a Brookfield RVT viscometer at a temperature of 25° C. (spindle no 6, 5 rpm)

The result are shown in Table 6

TABLE 6

| (UNIT: mPa · s) | Polymer (%) | A | B | C | D |
|---|---|---|---|---|---|
| Viscosity(Temperature 25° C., Brookfield RVT viscometer, spindle no 6, 5 rpm | 1% in water | 80000 | 70000 | 62000 | 72000 |
| | 1.5% in water | 106000 | 100000 | 96000 | 112000 |
| | 1% in waterAdjust to pH 12with NaOH | 27000 | 9200 | 1600 | 74000 |
| | 1.5% in water + 0.1% NaCl | 24800 | 25000 | 6300 | 74000 |
| | 1.5% in waterAdjust to pH 4with lactic acid | 90000 | 21600 | 84000 | 200Precipitation |
| | 1% in water + 3% Dihydroxyacetone | 53000 | 28000 | 32000 | 400Yellow color |
| | 0.75% in water + 2% H₂O₂ | 52000 | 46000 | 29000 | 37000 |

A: Copolymer of acryloyl morpholine/sodium acrylate/sodium 2-acrylamido-2-methyl-propane-sulfonate according to present invention
B: Copolymer of sodium acrylate/sodium 2-acrylamido-2-methylpropane-sulfonate according to European Patent No. 1047716

TABLE 6-continued

| (UNIT: mPa · s) | Polymer (%) | A | B | C | D |
|---|---|---|---|---|---|

C: Copolymer of Hydroxyethyl acrylate/sodium 2-acrylamido-2-methyl-propane-sulfonate according to European Patent No. 1369435
D: Copolymer of sodium acrylate/beheneth 25 methacrylate according to PCT publication No. WO 02/100374

These results demonstrate that the composition A which is the subject of the present invention have better properties that the product B, C, D of the prior art.

Examples of Cosmetic Formulations Based on Water in Oil Polymeric Emulsions of the Invention Example 1: Gel Cream A composition of a gel cream according to Manufacturing Example 1 was shown in Table 7. Materials of the following A in Table 7 were mixed with each other in a container and were heated to 70° C., materials of the following B in Table 7 were added and were emulsified by a homogenizer with 4000 rpm for 5 minutes, and a material of the following C in Table 7 was added and emulsified by a homogenizer with 4000 rpm for 3 minutes. Thereby, the gel cream was manufactured, and the manufactured gel cream was white, had a cream type, had a viscosity of 20000 mPa·s, and had pH of 5.62.

TABLE 7

| A | Water | 80.85% |
|---|---|---|
| | Coco glucoside and coconut alcohol | 4.50% |
| | EDTA-2Na | 0.05% |
| | Cyclomethicone | 10.00% |
| | Phenoxy ethanol | 0.20% |
| B | Glycerine | 3.00% |
| | Xanthan gum | 0.20% |
| C | the composition of Embodiment 1 to 6 | 1.20% |

Example 2: Sun Cream

A composition of a sun cream according to manufacturing Example 2 was shown in Table 8. Materials of the following A in Table 8 were mixed with each other in a container and were heated to 70° C., materials of the following B and C in Table 8 were added and were emulsified by a homogenizer with 4000 rpm for 5 minutes, a material of the following D in Table 8 was added and emulsified by a homogenizer with 4000 rpm for 3 minutes, was cooled to 45° C., and materials of the following E in Table 8 was added. Thereby, the sun cream was manufactured, and the manufactured sun cream had a viscosity of 132,000 mPa·s (Brookfield RVT, No 6, 5 rpm) and had pH of 7.7.

TABLE 8

| | | |
|---|---|---|
| A | Water | 50.25% |
| | Tetrasodium EDTA | 0.20% |
| | Potassium cetylphosphate | 0.50% |
| | Xanthan gum | 0.15% |
| | Veegum HV | 1.00% |
| B | Glyceryl stearate and PEG-100 stearate | 3.20% |
| | Cetostearyl alcohol | 1.00% |
| | Isononyl isononanoate | 10.00% |
| | Glycerin | 7.00% |
| | Octyl methoxycinnamate | 7.50% |
| | Octocrylene | 10.00% |
| | Avobenzone | 2.00% |
| C | Cyclopentasiloxane | 5.00% |
| D | the composition of Embodiment 1 to 6 | 1.20% |
| E | Phenoxy ethanol | 0.30% |
| | 1,2-hexandiol | 0.50% |
| | Tocopherol acetate | 0.10% |
| | Fragrance | 0.10% |

Example 3: Moisturizing Cream

A composition of a moisturizing cream according to manufacturing Example 3 was shown in Table 9. Materials of the following A in Table 9 were mixed with each other and were heated to 70° C. in a container, and materials of the following B in Table 9 were mixed with each other were heated to 70° C. in another container, the mixed materials of the following B in Table 9 was added into the mixed materials of the following A in Table 9, the mixture was emulsified by a homogenizer with 4000 rpm for 5 minutes, a material of the following C in Table 9 was added and emulsified by a homogenizer with 4000 rpm for 3 minutes, was cooled to 45° C., and a material of the following D in Table 9 was added. Thereby, the moisturizing cream was manufactured, and the manufactured moisturizing cream had a viscosity of 60,000 mPa·s (Brookfield RVT, No 6, 5 rpm) and had pH of 5.5.

TABLE 9

| | | |
|---|---|---|
| A | Water | 80.17% |
| | Glycerin | 5.00% |
| | PEG-8 | 0.50% |
| | EDTA-2NA | 0.03% |
| B | Beeswax | 1.00% |
| | Glyceryl stearate | 1.50% |
| | Stearic acid | 2.00% |
| | PEG-40 Hydrogenated castor oil | 1.00% |
| | Caprylic/capric triglyceride | 5.00% |
| | Polysorbate 80 | 0.60% |
| | Sorbitan sesquioleate | 0.60% |
| | Cyclopentasiloxane | 1.00% |
| C | the composition of Embodiment 1 to 6 | 1.20% |
| D | Fragrance | 0.40% |

Example 4: Mask Sheet Solution for the Face

A composition of a mask sheet solution for the face according to manufacturing Example 4 was shown in Table 10. Materials of the following A in Table 10 were mixed with each other and were heated to 70° C. in a container, and materials of the following B in Table 10 were mixed with each other were heated to 70° C. in another container, the mixed material of the following B in Table 10 was added into the mixed material of the following A in Table 10, the mixture was emulsified by a homogenizer with 4000 rpm for 5 minutes, a material of the following C in Table 10 was added and emulsified by a homogenizer with 4000 rpm for 3 minutes, was cooled to 45° C., and a material of the following D in Table 10 was added. Thereby, the mask sheet solution for the face was manufactured, and the manufactured immersion solution of the mask sheet had a viscosity of 1,400 mPa·s (Brookfield RVT, No 6, 5 rpm) and had pH of 6.4.

TABLE 10

| | | |
|---|---|---|
| A | Water | 86.23% |
| | EDTA-2NA | 0.02% |
| | Allantoin | 0.50% |
| | Niacinamide | 2.00% |
| | Glycerin | 3.00% |
| | Hyaluronic acid (1%) | 0.50% |
| | 1,3-Butylene glycol | 5.00% |
| B | PEG-60 Hydrogenated castor oil | 1.00% |
| | Bis-PEG-18 methyl etherdimethyl silane | 0.50% |
| C | the composition of Embodiment 1 to 6 | 1.10% |
| D | Phenoxy ethanol | 0.40% |
| | Ethylhexyl glycerin | 0.10% |
| | Fragrance | 0.10% |

Example 5: AHA Cream

A composition of an AHA cream according to manufacturing Example 5 was shown in Table 11. Materials of the following A in Table 11 were mixed with each other and were heated to 70° C. in a container, and materials of the following B in Table 11 were mixed with each other were heated to 70° C. in another container, the mixed material of the following B in Table 11 was added into the mixed material of the following A in Table 11, the mixture was emulsified by a homogenizer with 4000 rpm for 5 minutes, a material of the following C in Table 11 was added and emulsified by a homogenizer with 4000 rpm for 3 minutes, was cooled to 45° C., and a material of the following D in Table 11 was added. Thereby, the AHA cream was manufactured, and the manufactured moisturizing cream had a viscosity of 30,000 mPa·s (Brookfield RVT, No 6, 5 rpm) and had pH of 3.81.

TABLE 11

| | | |
|---|---|---|
| A | Water | 80.45% |
| | Citric acid | 1.50% |
| | Triethanolamine | 0.90% |
| B | Cetearyl olivate/sorbitan olivate | 4.00% |
| | Glyceryl stearate/PEG-100 stearate | 1.00% |
| | Isononyl isononanoate | 10.00% |
| | Methyl paraben | 0.20% |
| | Propyl paraben | 0.10% |
| | Butyl paraben | 0.10% |
| C | the composition of Embodiment 1 to 6 | 1.50% |
| D | Fragrance | 0.25% |

Example 6: Care Cream

A composition of a care cream according to manufacturing Example 6 was shown in Table 12. Materials of the following A in Table 12 were mixed with each other in a container and were heated to 70° C., materials of the following B in Table 12 were added and were emulsified by a homogenizer with 4000 rpm for 5 minutes, and a material of the following C in Table 12 was added and emulsified by a homogenizer with 4000 rpm for 3 minutes. Thereby, the care cream was manufactured, and the manufactured care cream was white, had a cream type, had a viscosity of 48000 mPa·s, and had pH of 5.88.

TABLE 12

| A | Water | Qsp 100.0% |
|---|---|---|
|   | Glycerine | 3.0% |
|   | EDTA-2Na | 0.1% |
|   | Xanthan gum | 0.3% |
| B | Cetearyl alcohol (Lanette O) | 2.0% |
|   | Cetearyl alcohol and Cetearyl glucoside(Montanov 68) | 1.5% |
|   | Dimethicone (200F/100 cs) | 10.0% |
|   | Phenoxy ethanol | 1.0% |
| C | the composition of Embodiment 1 to 6 | 1.0% |

Example 7: Fluid Emulsion with High pH

A composition of a fluid emulsion with high pH according to manufacturing Example 7 was shown in Table 13. Materials of the following A in Table 13 were mixed with each other in a container materials of the following B in Table 13 were added with mixing by a mechanical stirrer until pH 10 and were emulsified by a mechanical stirrer with 400 rpm for 20 minutes. Thereby, the care cream was manufactured, and the manufactured care cream was white, had a cream type, had a viscosity of 43000 mPa·s, and had pH of 10.1.

TABLE 13

| A | Water | 93.5% |
|---|---|---|
|   | Liquid paraffin | 5.0% |
|   | the composition of Embodiment 1 to 6 | 1.5% |
| B | 10% NaOH in water | Until pH 10 |

Example 8: Slimming Gel

A composition of a slimming gel according to manufacturing Example 8 was shown in Table 14. Materials of the following A in Table 14 were mixed with each other in a container, and were heated to 70° C., the mixture was emulsified by a homogenizer with 4000 rpm for 5 minutes. Thereby, the slimming gel was manufactured, and the manufactured slimming gel was white, had a cream type, had a viscosity of 98000 mPa·s, and had pH of 7.26.

TABLE 14

| A | Water | 61.9% |
|---|---|---|
|   | Ethanol | 30.0% |
|   | Menthol | 0.1% |
|   | Caffeine | 3.0% |
|   | Phenoxy ethanol | 1.0% |
|   | the composition of Embodiment 1 to 6 | 4.0% |

Example 9: Shampoo

A composition of a care cream according to manufacturing Example 9 was shown in Table 15. Materials of the following A in Table 15 were mixed with each other in a container and were heated to 70° C., the mixture was mixed by a homogenizer with 4000 rpm for 5 minutes, materials of the following B in Table 15 were added and were emulsified by a homogenizer with 4000 rpm for 5 minutes, and a materials of the following C in Table 15 were added with mixing by a mechanical stirrer until pH 7. Thereby, the shampoo was manufactured, and the manufactured shampoo was white, had a viscosity of 6600 mPa·s, and had pH of 7.01.

TABLE 15

| A | Water | Qsp 100.0% |
|---|---|---|
|   | 30% Sodium lauryl ether(2) sulfate | 35.0% |
|   | 30% Cocamidopropyl betaine | 3.0% |
|   | Cocamide MEA | 4.0% |
|   | the composition of Embodiment 1 to 6 | 4.0% |
| B | Phenoxy ethanol | 1.0% |
|   | Fragrance | 0.3% |
| C | 10% NaOH in water | Qs until pH 7 |

The above described features, configurations, effects, and the like are included in at least one of the embodiments of the present invention, and should not be limited to only one embodiment. In addition, the features, configurations, effects, and the like as illustrated in each embodiment may be implemented with regard to other embodiments as they are combined with one another or modified by those skilled in the art. Thus, content related to these combinations and modifications should be construed as being included in the scope and spirit of the invention as disclosed in the accompanying claims.

The invention claimed is:

1. A water-in-oil polymeric emulsion composition suitable for use in a cosmetic, dermo-cosmetic, or pharmaceutical formulation, the composition comprising:
    (a) 25 to 65 wt % of a cross-linked polymer;
    (b) 15 to 40 wt % of at least one oil;
    (c) 1 to 12 wt % of a least one surfactant or polymeric surfactant; and
    (d) 1 to 40 wt % of water,
    wherein (a) the cross-linked polymer is polymerized by using 35 to 85 mol % of a 2-acrylamido-2-methylpropane-sulfonic acid totally or partially salified by an alkali metal or ammonium, 10 to 50 mol % of acryloyl morpholine, 2 to 25 mol % of an acrylic acid totally or partially salified by an alkali metal or ammonium, and 0.005 to 1 mol % (mole of cross-linker/mole of monomer) of a polyethylenic monomer used as a cross-linking agent,
    wherein the emulsion composition does not include acrylamide.

2. The water-in-oil polymeric emulsion composition according to claim 1, wherein (a) the cross-linked polymer is polymerized by using 40 to 80 mol % of the 2-acrylamido-2-methylpropane-sulfonic acid totally or partially salified by the alkali metal or ammonium, 15 to 45 mol % of the acryloyl morpholine, 2 to 15 mol % of the acrylic acid totally or partially salified by the alkali metal or ammonium, and 0.005 to 1 mol % of the polyethylenic monomer.

3. The water-in-oil polymeric emulsion composition according to claim 2, wherein (a) the cross-linked polymer is polymerized by using 50 to 70 mol % of the 2-acrylamido-2-methylpropane-sulfonic acid totally or partially salified by the alkali metal or ammonium, 20 to 40 mol % of the acryloyl morpholine, 2 to 10 mol % of the acrylic acid totally or partially salified by the alkali metal or ammonium, and 0.005 to 1 mol % of the polyethylenic monomer.

4. The water-in-oil polymeric emulsion composition according to claim 1, wherein the 2-acrylamido-2-methylpropane-sulfonic acid is a 2-acrylamido-2-methylpropane-sulfonic acid totally or partially salified by sodium, and wherein the acrylic acid is an acrylic acid totally or partially salified by sodium.

5. The water-in-oil polymeric emulsion composition according to claim 1, wherein (a) the cross-linked polymer is included in an amount of 30 to 50 wt %.

6. The water-in-oil polymeric emulsion composition according to claim 1, wherein (b) the oil is included in an amount of 20 to 30 wt %.

7. The water-in-oil polymeric emulsion composition according to claim 1, wherein (d) the water is included in an amount of 15 to 35 wt %.

8. The water-in-oil polymeric emulsion composition according to claim 1, wherein (c) there is at least a surfactant having a HLB of 3 to 7 or a polymeric surfactant having a HLB of 3 to 7 in an amount of 2 to 10%.

9. The water-in-oil polymeric emulsion composition according to claim 8, wherein (c) there are at least two surfactants or polymeric surfactants; one or more which a HLB of 3 to 7 and another one having a HLB of 10 to 16.

10. The water in oil polymeric emulsion composition according to claim 8 wherein (c) there are at least one surfactant having a HLB of 3 to 7 and one polymeric surfactant having a HLB of 3 to 7 and a surfactant having a HLB of 10 to 16.

11. The water-in-oil polymeric emulsion composition according to claim 1, wherein (b) the oil comprises at least one selected from the group consisting of a mineral oil, a white mineral oil, a synthetic oil, and a natural oil.

12. The water-in-oil polymeric emulsion composition according to claim 11, wherein (b) the oil comprises a natural oil of fatty alcohol ether or fatty esters.

13. The water-in-oil polymeric emulsion composition according to claim 11, wherein (b) the oil comprises dioctyl ether.

14. The water-in-oil polymeric emulsion composition according to claim 8, wherein the surfactant having the HLB of 3 to 7 comprises sorbitan ester and the polymeric surfactant having the HLB of 3 to 7 comprises a block copolymeric ester of a hydroxystearic acid and ethylene glycol.

15. The water-in-oil polymeric emulsion composition according to claim 8, wherein the surfactant having the HLB of 10 to 16 comprises polyglycerol ester or alkyl polyglucoside.

16. The water-in-oil polymeric emulsion composition according to claim 15, wherein the polyglycerol ester comprises decaglycerol dilaurate.

17. The water-in-oil polymeric emulsion composition according to claim 9, wherein the surfactant having the HLB of 10 to 16 is included in an amount of 1 to 6 wt %.

18. The water in oil polymeric emulsion composition according to claim 17, wherein the surfactant having the HLB of 10 to 16 is included in an amount of 3 to 5%.

19. The water-in-oil polymeric emulsion composition according to claim 1, wherein the polyethylenic monomer is included in an amount of 0.01 to 0.6 mol %.

20. The water-in-oil polymeric emulsion composition according to claim 19, wherein the polyethylenic monomer is included in an amount of 0.02 to 0.4 mol %.

21. The water-in-oil polymeric emulsion composition according to claim 1, wherein the polyethylenic monomer comprises at least one selected from the group consisting of methylene-bis-acrylamide, ethylene glycol dimethacrylate, diethylene glycol dimethacrylate, triallylamine, trimethylol propane tri(meth)acrylate, diallyl urea, tetra allyl oxy ethane, a diallyl oxy acetic acid, allyl penta erythritol, allyl sucrose, and trimethylolpropane diallyl ether.

22. The water-in-oil polymeric emulsion composition according to claim 21, wherein the polyethylenic monomer comprises the methylene-bis-acrylamide, or a triallylamine, or a mixture thereof.

* * * * *